United States Patent
Pulford

(10) Patent No.: US 11,433,037 B2
(45) Date of Patent: Sep. 6, 2022

(54) ORAL DOSAGE FORM CONTAINING A FAST RELEASE EXTERIOR COATING

(71) Applicant: GlaxoSmithKline Consumer Healthcare Holdings (US) LLC, Wilmington, DE (US)

(72) Inventor: Christopher Joseph Pulford, Lincoln, NE (US)

(73) Assignee: GLAXOSMITHKLINE CONSUMER HEALTHCARE HOLDINGS (US) LLC, Wilmington, DE (US)

(*) Notice: Subject to any disclaimer, the term of this patent is extended or adjusted under 35 U.S.C. 154(b) by 0 days.

(21) Appl. No.: 15/641,448

(22) Filed: Jul. 5, 2017

(65) Prior Publication Data
US 2018/0008562 A1    Jan. 11, 2018

Related U.S. Application Data

(60) Provisional application No. 62/358,223, filed on Jul. 5, 2016.

(51) Int. Cl.

| A61K 31/167 | (2006.01) |
|---|---|
| A61K 9/20 | (2006.01) |
| A61K 31/485 | (2006.01) |
| A61K 9/00 | (2006.01) |
| A61K 9/28 | (2006.01) |
| A61K 31/137 | (2006.01) |
| A61K 31/138 | (2006.01) |

(52) U.S. Cl.
CPC .......... *A61K 31/167* (2013.01); *A61K 9/0053* (2013.01); *A61K 9/2054* (2013.01); *A61K 9/2826* (2013.01); *A61K 9/2866* (2013.01); *A61K 9/2886* (2013.01); *A61K 31/137* (2013.01); *A61K 31/138* (2013.01); *A61K 31/485* (2013.01)

(58) Field of Classification Search
CPC combination set(s) only.
See application file for complete search history.

(56) References Cited

U.S. PATENT DOCUMENTS

| 4,789,546 | A | 12/1988 | Medri |
| 5,098,715 | A | 3/1992 | McCabe et al. |
| 5,658,589 | A * | 8/1997 | Parekh ............ A61J 3/005 424/463 |
| 5,807,580 | A | 9/1998 | Luber |
| 6,365,215 | B1 | 4/2002 | Grainger et al. |
| 6,432,441 | B1 | 8/2002 | Bealin-Kelly et al. |
| 6,596,298 | B2 * | 7/2003 | Leung ............ A23G 3/50 424/405 |
| 6,620,791 | B1 | 9/2003 | Cooper et al. |
| 6,899,901 | B2 | 5/2005 | Nakatsu et al. |
| 7,374,781 | B2 | 5/2008 | Zhang et al. |
| 7,785,650 | B2 | 8/2010 | Gulian |
| 9,161,890 | B2 | 10/2015 | Boyd et al. |
| 2002/0119196 | A1 * | 8/2002 | Parikh ............ A61K 9/0056 424/472 |
| 2003/0072731 | A1 * | 4/2003 | Gulian ............ A61K 9/2853 424/70.13 |
| 2005/0123601 | A1 | 6/2005 | Mane et al. |
| 2005/0196517 | A1 | 9/2005 | Hodanko et al. |
| 2006/0034936 | A1 | 2/2006 | Lakkis et al. |
| 2006/0127473 | A1 * | 6/2006 | Nichols ............ A61K 9/2054 424/464 |
| 2007/0036733 | A1 | 2/2007 | Spence et al. |
| 2007/0148103 | A1 | 6/2007 | Harvey |
| 2007/0231387 | A1 | 10/2007 | Levi et al. |
| 2007/0275135 | A1 | 11/2007 | Aziz et al. |
| 2008/0000614 | A1 | 1/2008 | Maurel et al. |
| 2008/0131467 | A1 | 6/2008 | Nelson et al. |
| 2008/0317677 | A1 * | 12/2008 | Szymczak ............ A61K 9/2072 424/10.2 |
| 2009/0208568 | A1 | 8/2009 | Hannetel et al. |
| 2010/0330169 | A1 | 12/2010 | Bunick et al. |
| 2011/0015227 | A1 | 1/2011 | Desierto et al. |
| 2012/0207831 | A1 | 8/2012 | Stella et al. |
| 2012/0321727 | A1 | 12/2012 | Windschauer et al. |
| 2014/0010768 | A1 | 1/2014 | Chambers et al. |
| 2014/0079740 | A1 | 3/2014 | Salama |

FOREIGN PATENT DOCUMENTS

| DE | 19962251 A1 | 9/2001 |
| EP | 2233134 A1 | 9/2010 |
| WO | WO 9702273 A1 | 1/1997 |
| WO | WO 9847483 A1 | 10/1998 |
| WO | WO 9852545 A1 | 11/1998 |
| WO | WO 2011/056702 A2 | 5/2011 |
| WO | WO 2013/103318 A1 | 7/2013 |

OTHER PUBLICATIONS

OTHER PUBLICATIONS https://www.drugs.com/otc/131559/be105f3f-0205-417b-894a-e5d8fcfc9b94-01.jpg.
https://www.drugs.com/otc/131560/d1792be4-f6e2-4f62-ae7a-c016722f6202-01.jpg.
PCT Search Report and Written Opinion.
"Opadry(R) II Complete Film Coating System 30B120016 Yellow", Colorcon certificate of Analysis; May 4, 2016 (May 4, 2016), pp. 1-2, XP002797238, Retrieved from the Internet: URL:https://www.stobec.com/DATA/PRODUIT/2203-v-certificateopadryyellow.pdf [retrieved on Jan. 28, 2020] * the whole document*.

* cited by examiner

Primary Examiner — Jeffrey T. Palenik
(74) Attorney, Agent, or Firm — Diane E. Furman; Roshni A. Sitapara

(57) ABSTRACT

Aspects of the present invention are directed to an oral dosage form comprising a core containing one more active ingredients and a fast-release exterior coating. The fast release exterior coating includes a water soluble polymer; a saccharide or sugar alcohol, or a combination thereof, and a flavoring. The flavoring may be a warming sensate that is released in the oral cavity of the user after inserting the dosage form in his or her mouth.

31 Claims, 1 Drawing Sheet

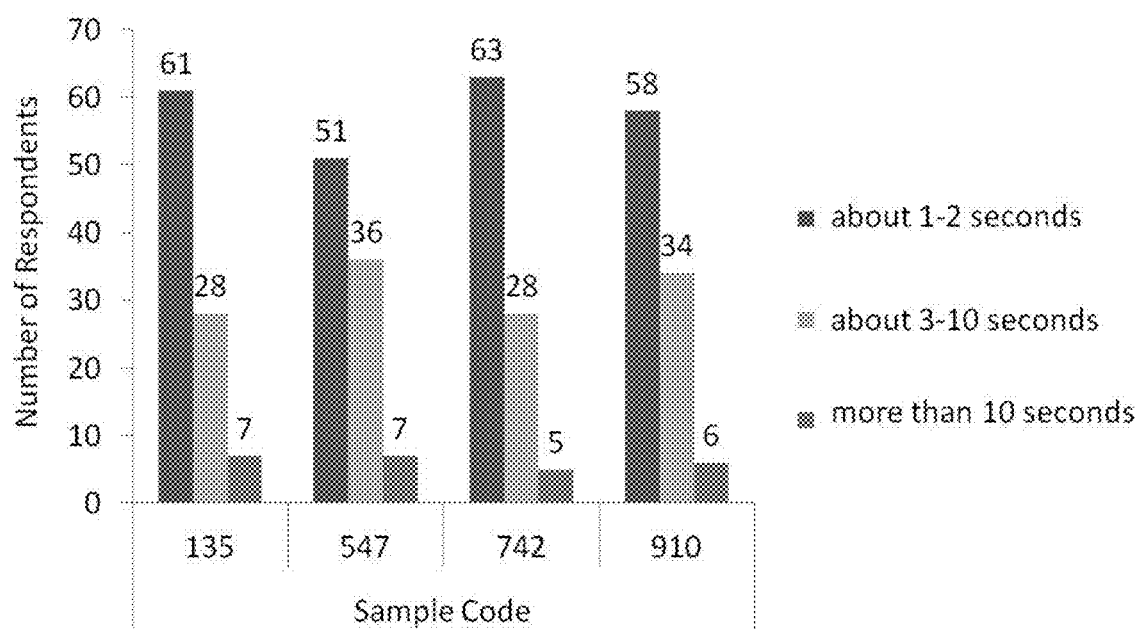

ORAL DOSAGE FORM CONTAINING A FAST RELEASE EXTERIOR COATING

TECHNOLOGY FIELD

Aspects of the present invention are directed to an oral dosage form containing a fast-release exterior coating containing flavorings, and, in particular, an oral dosage form containing a fast-release coating that allows for the release of a sensate in the oral cavity of a user.

BACKGROUND

Oral dosage forms such as tablets, caplets, and capsules are commonly used to treat or alleviate symptoms related to various ailments. An active ingredient or multiple active ingredients are formulated into the dosage form such that upon administration, the user swallows the dosage form, the dosage form dissolves in the stomach of the user and the actives are absorbed and treat the user. It is also well known that dosage forms may be coated with various types of coatings to protect the dosage form from degradation or to modify the release profile of the dosage form upon administration. For example, a dosage form may be coated with an enteric coating to prevent the dosage form from dissolving in the stomach but rather dissolve in the small intestine where the pH is higher.

One of the drawbacks of oral dosage forms is that because they are administered orally and swallowed by the user, the user may not immediately feel the effect of the medicine. Some oral dosage forms are designed to dissolve in the oral cavity, such as for example, nicotine-containing lozenges. In these instances, the lozenges need to be held in the mouth for an extended period of time for it to completely dissolve. The nicotine is then absorbed through the buccal cavity of the user and in a short period of time, the user experiences the effect of the active ingredient.

In many instances, however, a dosage form as mentioned above is not practical. First, many active ingredients may not be absorbed through the buccal cavity for various reasons, such as, for example, the active is insoluble at the pH of the oral cavity. On a more practical level, however, many users do not want to hold a tablet or caplet in their mouth for an extended period of time leading to user compliance issues.

Because of these aforementioned issues, it would be preferable to coat an oral dosage form with an exterior coating that would quickly release a flavor or sensate in the oral cavity to provide an immediate benefit to the user. The benefit may be a physical benefit, such as a soothing effect. For example, if the user is taking an oral dosage form to treat symptoms of cold and/or flu, the physical benefit may be a soothing effect on a sore throat of the user. In other instances, the benefit may be psychological. For example, a tingling or warming sensation may be a trigger to the user that the medicine is working or will soon be working to reduce or eliminate their symptoms. When the oral dosage form is intended to be dissolved in the oral cavity, such as where nicotine is the active ingredient, it would be beneficial to coat the lozenge with a fast release layer that releases a flavor or sensate prior to the nicotine being release. Such release of flavor or sensate my result in craving relief but may also result in preparing the oral cavity for the strong, unpleasant flavor of nicotine. Providing such benefits to the user has proven to be difficult because prior attempts have resulted in exterior coatings that did not quickly enough release a flavor or sensate to impart a benefit or experience to the user before the user swallows the dosage form. Thus, a coating for an orally administered dosage form that could more quickly impart a benefit or experience to a user before the user swallows the dosage form would be highly desirable.

SUMMARY

Aspects of the present invention are directed to an oral dosage form comprising: a core containing one or more active ingredients; and a fast-release, exterior coating comprising: a water soluble polymer; a saccharide or sugar alcohol or combination thereof; and a flavoring.

Additional aspects of the present invention are directed to an oral dosage form comprising: a core containing acetaminophen, dextromethorphan, and phenylephrine; an intermediate coating comprising hydroxypropylmethylcellulose; and a fast-release exterior coating comprising: hydroxypropylmethylcellulose; maltodextrin; and a warming sensate.

Additional aspects of the present invention are directed to an oral dosage form comprising: a core containing between about 300 mg and about 400 mg acetaminophen, between about 5 mg and about 15 mg dextromethorphan, and between about 2.5 mg and about 7.5 mg phenylephrine; an intermediate coating comprising between about 10 mg and about 20 mg hydroxypropylmethylcellulose; and a fast-release exterior coating comprising: between about 2 mg and about 6 mg hydroxypropylmethylcellulose; between about 3 mg and about 5 mg maltodextrin; and between about 0.5 mg and about 2.5 mg a warming sensate.

Additional aspects of the present invention are directed to an oral dosage form comprising: a core containing acetaminophen, diphenhydramine, and phenylephrine; an intermediate coating comprising hydroxypropylmethylcellulose; and a fast-release exterior coating comprising: hydroxypropylmethylcellulose; maltodextrin; and a warming sensate.

Additional aspects of the present invention are directed to an oral dosage form comprising: a core containing between about 300 mg and about 400 mg acetaminophen, between about 10 mg and about 15 mg diphenhydramine, and between about 2.5 mg and about 7.5 mg phenylephrine; an intermediate coating comprising between about 10 mg and about 20 mg hydroxypropylmethylcellulose; and a fast-release exterior coating comprising: between about 2 mg and about 6 mg hydroxypropylmethylcellulose; between about 3 mg and about 5 mg maltodextrin; and between about 0.5 mg and about 2.5 mg a warming sensate.

Additional aspects of the present invention are directed to a method comprising: inserting an oral dosage form of any of the preceding claims into the oral cavity of a user; holding the oral dosage form in the oral cavity of the user until a sensorial experience is observed by the user; and swallowing the oral dosage form.

Additional aspects of the present invention are directed to a method of treating the symptoms of cold and/or flu, allergies, or nicotine craving comprising administering to a human subject in need thereof an oral dosage form as described herein.

Additional aspects of the present invention are directed to a method of treating the symptoms of cold and/or flu comprising administering to a human subject in need thereof an oral dosage form as described herein.

Additional aspects of the present invention are directed to use of an oral dosage form as described here for the treatment of symptoms of cold and/or flu; allergies, or nicotine cravings.

Additional aspects of the present invention are directed to use of an oral dosage form as described here for the treatment of symptoms of cold and/or flu.

BRIEF DESCRIPTION OF THE DRAWINGS

FIG. 1 shows a graph of how quickly respondents experienced sensate from oral dosage forms of the present invention.

DETAILED DESCRIPTION

Aspects of the present invention are directed to an oral dosage form comprising a core containing one more active ingredients and a fast-release exterior coating. The fast release exterior coating includes a water soluble polymer; a saccharide or a sugar alcohol, or a combination thereof; and a flavoring.

The presently disclosed oral dosage form is an improvement over prior oral dosage forms at least because the fast release exterior coating allows for a flavoring to be released more quickly than traditional coated oral dosage forms. Such increased speed in flavor release may provide a benefit to users who are experiencing a need for quick relief of symptoms. Although the flavoring may not necessarily provide relief of symptoms, it is thought that a quick releasing sensate may provide a soothing effect to the user, or may distract the user from a craving or from symptoms of an ailment from which they are suffering. Additionally, the sensate may provide the user with an indication that the active ingredient(s) in the dosage form is/are working or will soon be working.

The fast release exterior coating comprises a water soluble polymer; a saccharide or a sugar alcohol, or combination thereof; and a flavoring. Unless otherwise stated, the water soluble polymer may be a single water soluble polymer or a mixture of water soluble polymers. Suitable water soluble polymers may include, for example, an alkylcellulose, hydroxyalkylcellulose, hydroxyalkyl alkylcellulose, polyalkylene oxide, carboxyalkylcellulose esters methacrylate copolymers; polyvinylalcohol; polyvinylpyrrolidone, a copolymer of polyvinylpyrrolidone with vinyl acetate; combinations of polyvinylalcohol and polyvinylpyrrolidone and copolymers of ethylene oxide and propylene oxide, or combinations thereof. In certain embodiments, an alkylcellulose, hydroxyalkylcellulose, hydroxyalkyl alkylcellulose, polyalkylene oxide, or combinations thereof. In certain embodiments, the water, soluble polymer is an alkyl cellulose or an hydroxyalkylcellulose. In a preferred embodiment, the water soluble polymer is a hydroxyalkylcellulose. In a more preferred embodiment, the water soluble polymer is hydroxypropylmethylcellulose. In some embodiments, the water soluble polymer is a combination of a hydroxyalkylcelloluse and polyethylene glycol. In a preferred embodiment, the water soluble polymer is a combination of hydroxypropylmethylcelloluse and polyethylene glycol. The water soluble polymer(s) may be present in the coating in an amount from between about 10% (w/w) and about 90% (w/w), preferably between about 15% (w/w) and about 50% (w/w), and more preferably between about 20% (w/w) and about 25% (w/w).

The fast release exterior coating also comprises a saccharide or a sugar alcohol, or a combination thereof. Unless otherwise stated, the saccharide or sugar alcohol may be a single saccharide or sugar alcohol or a mixture of saccharides or sugar alcohols. Suitable saccharides may include a monosaccharide, disaccharide, polysaccharide, or mixtures thereof. For example, the saccharide may include maltose, fructose, glucose, trehalose, sucrose, dextrose, maltodextrin, polydextrose or a mixture thereof. In a preferred embodiment, the fast release exterior coating contains only a saccharide. In a more preferred embodiment, the fast release exterior coating contains only maltodextrin. Suitable sugar alcohols may include, for example, sorbitol, mannitol, xylitol, isomalt, erythritol, lactitol, or mixtures thereof.

The saccharide, sugar alcohol, or combination thereof, may be present in the coating in an amount between about 1% (w/w) and about 50% (w/w), preferably between about 10% (w/w) and about 30% (w/w), and more preferably between about 20% (w/w) and about 25% (w/w).

The fast release exterior coating also includes a flavoring. The flavoring may be present in the coating in an amount from between about 0.01% (w/w) to about 5% (w/w), preferably between about 0.05% (w/w) to about 2.5% (w/w), and more preferably between about 0.09% (w/w) to about 1.0% (w/w).

Preferably, the flavoring includes a sensate. As used herein, a sensate refers to a compound or combination of compounds that provides a sensorial experience to a user, and, in particular compounds or combinations of compounds that stimulate the trigeminal nerve to induce a warming, cooling, salivating or pungent sensation to a user as described in US Publication No. 2011/0015227 and International Patent Publication No. WO 2007/144800. The sensorial experience may be a warming experience, or it may be a cooling experience. In a preferred embodiment, the sensate is a warming sensate. Suitable warming sensates may include, for example, those described in US2011/0015227, WO2007/144800, capsaicin, piperine, dihydrocapsaicin, chavicine, nonivamide, cis-pellitorine, ethyl ether, vanillyl propyl ether, vanillin propylene glycol acetal, ethyl vanillin propylene glycol acetal, gingerol, vanillyl butyl ether, 4-(I-menthoxy-methyl)-2-phenyl-1,3-dioxolane, 4-(I-menthoxy-methyl)-2-(3',4'-dihydroxy-phenyl)-1,3-dioxolane, 4-(I-menthoxy-methyl)-2-(2'-hydroxy-3'-methoxyphenyl)-1,3-dioxolane, 4-(I-menthoxy-methyl)-2-(4'-methoxyphenyl)-1,3-dioxolane, 4-(I-menthoxy-methyl)-2-(3',4'-methylenedioxy-phenyl)-1,3-dioxolane, hot pepper oil, capsicum oleoresin, ginger oleoresin, nonyl acid vanillylamide, and 4-(I-menthoxy-methyl)-2-(3'-methoxy-4'-hydroxyphenyl)-1,3-dioxolane, Art Sensate 553409 T (Firmenich), or combinations thereof. Art Sensate 553409T (Firmenich) comprises 10-25% of warming sensate (w/w).

Suitable cooling sensates may include, for example, those described in US2011/0015227, WO2007/144800, isopulegole, 3-(I-menthoxy)propan-1 2-diol, p-menthan-3,8-diol, 6-isopropyl-9-methyl-1,4-dioxaspiro-(4,5)-decane-2-methanol, menthyl succinate, alkaline earth salts of menthyl succinate, trimethyl cyclohexanol, N-ethyl-2-isopropyl-5-methylcyclohexane carboxamide, 3-(I-menthoxy)-2-methyl-propan-1,2-diol, mint oil, peppermint oil, wintergreen, menthone, menthone glycerin ketal, menthyl lactate, [1'R,2'S,5'R]-2-(5'-methyl-2'-(methylethyl)cyclohexyloxy)ethan-1-ol, [1'R,2'S,5'R]-3-(5'- methyl-2'-(methylethyl)cyclohexyloxy)propan-1-ol, [1'R,2'S,5'R]-4-(5'-methyl-2'-(methylethyl)cyclohexyloxy)butan-1-ol, spearmint, gardamide, N-substituted p-menthane carboxamides, menthoxypropan-1,2-diol, menthol and menthyl esters, such as Cooler #2 which is available from International Flavors & Fragrances in Hazlet, N.J., or combinations thereof.

In a preferred embodiment, the sensate is a warming sensate, preferably, Art Sensate 553409 T (Firmenich). As described above Art Sensates 553409T comprises 10-25% warming sensate. In a preferred embodiment, the sensate provides a sensorial experience in the oral cavity of the user.

The flavoring may also include a second flavor in addition to the sensate. Suitable flavors may include, for example, mint, menthol, peppermint, wintergreen, sweet mint, spearmint, vanillin, caramel, chocolate, coffee, cinnamon, clove, tobacco, citrus, lemon, lime, orange, grape, cherry, strawberry, fruit punch, honey, honey-lemon, other fruit flavors or mixtures thereof.

The water-soluble polymer; the saccharide or sugar alcohol, or combination thereof; and the flavoring are preferably evenly distributed throughout the fast release exterior coating. Likewise, the fast release exterior coating may be present on at least a portion of the core or it may be distributed about the entirety of the core, preferably the fast release exterior coating is evenly distributed about the entirety of the core. In certain embodiments, the fast release exterior coating may have a thickness of between about 10 µm and about 100 µm, preferably between about 40 µm and about 80 µm, more preferably between about 50 µm and about 70 µm. The coating may also have a weight of between about 0.5% (w/w) and about 20% (w/w) of the oral dosage form, preferably between about 1% (w/w) and about 10% (w/w) of the oral dosage form, and more preferably between about 2% (w/w) and about 5% (w/w) of the oral dosage form.

In certain embodiments, the fast release exterior coating may also include a preservative, solvent, sweetener, or combinations thereof. Suitable preservatives may include sodium benzoate, benzoic acid, propylparaben, methylparaben. In one embodiment, the preservative is benzoic acid. Suitable amounts of preservative in the fast release exterior coating may be between about 0.1% (w/w) and about 1% (w/w). Suitable solvents may include, for example, propylene glycol, glycerin, polyethylene glycol, polysorbate. In one embodiment, the solvent is Polysorbate 60 (NF) (Tween 60). Suitable amounts of solvent in the fast release exterior coating may be between about 1% (w/w) and about 10% (w/w). Suitable sweeteners may include, for example, aspartame, acesulfame K, sucralose, saccharin, stevia, sucrose. In one embodiment, the sweetener may be sucralose. Suitable amounts of sweetener in the fast release exterior coating may be between about 1% (w/w) and about 2% (w/w).

A benefit of the present invention over the prior art is the ability of the flavor, and in particular the sensate, to more quickly release from the fast release exterior coating than in traditional coatings. Traditionally, for oral dosage forms intended to be swallowed, users will not hold the dosage form in their mouth, but will, rather, immediately swallow the dosage form. If the sensate is still contained within the coating when the user swallows the dosage form, the sensate will not be experienced by the user in the mouth or throat as preferred. A faster release coating allows for the sensate to be experienced by the user in the oral cavity.

In some embodiments, the sensate is observed by the user within about 10 seconds after placing the oral dosage form in their mouth. In a preferred embodiment, the sensate is observed by the user within about 5 seconds after placing the oral dosage form in their mouth. In a more preferred embodiment, the sensate is observed by the user within about 3 seconds after placing the oral dosage form in their mouth. In a more preferred embodiment, the sensate is observed by the user within about 2 seconds after placing the oral dosage form in their mouth.

Oral dosage forms of the present invention also include a core containing one or more active ingredients. The core may be soluble or insoluble in the oral cavity. In certain embodiments, the core is insoluble in the oral cavity and/or is intended to be swallowed by the user. The core may be one of several generally known forms, such as, for example, a tablet, caplet, capsule, chewing gum, or lozenge. In a preferred embodiment, the core is a caplet.

The oral dosage form may have an overall weight of between about 250 mg and about 2,500 mg, or between about 500 mg and about 1,000 mg, or between about 600 mg and about 700 mg. In one embodiment, the oral dosage form has a weight of about 625 mg.

The core may contain one or more active ingredients. Suitable active ingredients may include, for example, actives that are traditional administered in an oral dosage form, such as, for example, analgesics, anti-inflammatories, decongestants, cough suppressants, expectorants, and antihistamines. In certain embodiments, the active ingredients may be acetaminophen, phenylephrine, pseudoephedrine, dextromethorphan, diphenhydramine, nicotine, guaifenesin, acetylcisteine, chlorpheniramine, cetirizine, levocetirizine, any salts thereof, or combinations thereof. In some embodiments, the core contains three active ingredients. The three active ingredients may be acetaminophen, phenylephrine, and dextromethorphan. In certain embodiments, the three active ingredients may be acetaminophen, phenylephrine HCl and dextromethorphan HBr. In other embodiments, the three active ingredients may be acetaminophen, phenylephrine, and diphenhydramine. In still other embodiments, the three active ingredients may be acetaminophen, phenylephrine HCl and diphenhydramine HCl.

In certain embodiments, the one or more active ingredients may be present in an amount of from between about 1 mg and about 1,000 mg. In embodiments wherein the core contains acetaminophen, it is present in an amount of between about 300 mg and about 650 mg. In a preferred embodiment, the acetaminophen is present in an amount of about 325 mg. In embodiments wherein the core contains phenylephrine, it is present in an amount of between about 2.5 mg and about 20 mg. In a preferred embodiment, the phenylephrine is present in an amount of about 5 mg. In embodiments wherein the core contains dextromethorphan, it is present in an amount of between about 5 mg and about 30 mg. In a preferred embodiment, the dextromethorphan is present in an amount of about 10 mg. In embodiments wherein the core contains diphenhydramine, it is present in an amount of between about 5 mg and about 40 mg. In a preferred embodiment, the diphenhydramine is present in an amount of about 12.5 mg.

Additionally, the core may contain a filler, a disintegrant, a glidant, a lubricant, an antioxidants, or combinations thereof as understood by one skilled in the art. Suitable fillers may include, for example, various grades of microcrystalline cellulose, such as Avicel PH101, Avicel PH102, & Avicel PH200; corn starch; or combinations thereof. In one embodiment, the filler is Avicel-PH102. The filler may be present in the core in an amount between about 10% (w/w) and about 50% (w/w) or between about 20% (w/w) and about 30% (w/w). Suitable disintegrants may include, for example, sodium starch glycolate [Explotab], crosslinked polyvinylpyrrolidone, corn starch, acacia, croscarmellose sodium [Ac-di-sol], sodium carboxymethylcellulose, veegum, alginates, or combinations thereof. In one embodiment, the disintegrant is Croscarmellose sodium. The disintegrant may be present in the core in an amount between about 1% (w/w) and about 10% (w/w), or between about 2% (w/w) and about 6% (w/w). Suitable glidants may include, for example, talc, corn starch, stearic acid, calcium stearate, polyethylene glycol, silicon dioxide, sodium stearyl fumarate, magnesium stearate, vegetable and mineral oils and mixtures thereof. In one embodiment, the glidant is silicon dioxide. The glidant may be present in the core in an amount between about 0.001% (w/w) and about 1% (w/w), or from about 0.005% (w/w) and about 0.1% (w/w). Suitable lubricants may include, for example, magnesium stearate, stearic acid and its pharmaceutically acceptable alkali metal salts, calcium stearate, sodium stearate, Cab-O-Sil, Syloid, sodium lauryl sulfate, sodium chloride, magnesium lauryl sulfate, talc, or combinations thereof. In one embodiment, the lubricant is stearic acid and magnesium stearate. The lubricant may be present in the core in an amount between about 0.1% (w/w) and about 2% (w/w), or between about 0.2% (w/w) and about 1% (w/w). Suitable antioxidants may include, for example, alpha tocopherol, beta tocopherol, gamma tocopherol, delta tocopherol, butylated hydroxytoluene (BHT), butylated hydroxyanisole (BHA), ascorbic acid, fumaric acid, malic acid, ascorbyl palmitate, propyl gallate, sodium ascorbate, sodium metabisulfite, or combinations thereof.

In some embodiments, the oral dosage form may further contain an intermediate coating between the core and the fast release exterior coating. In preferred embodiments, the intermediate coating dissolves slower than the fast release exterior coating. The intermediate coating may serve to prevent degradation of the active ingredients in the core. The intermediate coating may also serve to prevent the core from dissolving in the oral cavity. This may be particularly useful when the active ingredient has a bad taste in the mouth of the user. In instances where an interaction between the flavor molecules in the exterior coating may result in adverse interactions with the actives ingredients within the core, the intermediate coating may serve as a barrier between the flavor molecules and the active ingredients. The intermediate coating may comprise a water-soluble polymer, which may be the same or different than the water soluble polymer in the fast release exterior coating. Suitable water soluble polymers may include an alkylcellulose, hydroxyalkylcellulose, hydroxyalkyl alkylcellulose, polyalkylene oxide, carboxyalkylcellulose esters methacrylate copolymers; polyvinylalcohol; polyvinylpyrrolidone, a copolymer of polyvinylpyrrolidone with vinyl acetate; combinations of polyvinylalcohol and polyvinylpyrrolidone and copolymers of ethylene oxide and propylene oxide, or combinations thereof. In certain embodiments, an alkylcellulose, hydroxyalkylcellulose, hydroxyalkyl alkylcellulose, polyalkylene oxide, or combinations thereof. In certain embodiments, the water, soluble polymer is an alkyl cellulose or an hydroxyalkylcellulose. In a preferred embodiment, the water soluble polymer is a hydroxyalkylcellulose. In a more preferred embodiment, the water soluble polymer is hydroxypropylmethylcellulose. In some embodiments, the water soluble polymer is a combination of a hydroxyalkylcellulose and polyethylene glycol. In a preferred embodiment, the water soluble polymer is a combination of hydroxypropylmethylcelloluse and polyethylene glycol. The water soluble polymer(s) may be present from between about 50% (w/w) and about 100% (w/w) of the intermediate coating, or between about 90% (w/w) and about 100% (w/w) of the intermediate coating.

The intermediate coating may have a thickness of between about 10 μm and about 100 μm, or between about 50 μm and about 70 μm. The intermediate coating may have a weight of between about 1% (w/w) and about 10% (w/w) of the oral dosage form, or between about 2% (w/w) and about 5% (w/w) of the oral dosage form.

The intermediate coating may comprise a preservative, which may be the same or different than the preservatives in the fast release exterior coating. Suitable preservatives may include sodium benzoate, benzoic acid, propylparaben, methylparaben. In one embodiment, the preservative is benzoic acid. Suitable amounts of preservative in the intermediate coating may be between about 0.1% (w/w) and about 1% (w/w).

One embodiment of the present invention is directed to an oral dosage form comprising: a core containing acetaminophen, dextromethorphan, and phenylephrine; an intermediate coating comprising hydroxypropylmethylcellulose; and a fast-release exterior coating comprising: hydroxypropylmethylcellulose; maltodextrin; and a warming sensate.

Another embodiment of the present invention is directed to an oral dosage form comprising: a core containing between about 300 mg and about 400 mg acetaminophen, between about 5 mg and about 15 mg dextromethorphan, and between about 2.5 mg and about 7.5 mg phenylephrine; an intermediate coating comprising between about 10 mg and about 20 mg hydroxypropylmethylcellulose and polyethylene glycol; and a fast-release exterior coating comprising: between about 2 mg and about 6 mg hydroxypropylmethylcellulose and polyethylene glycol, between about 3 mg and about 5 mg maltodextrin; and between about 0.5 mg and about 2.5 mg warming sensate.

Another embodiment of the present invention is directed to an oral dosage form comprising: a core containing acetaminophen, diphenhydramine, and phenylephrine; an intermediate coating comprising hydroxypropylmethylcellulose; and a fast-release exterior coating comprising: hydroxypropylmethylcellulose, maltodextrin, and a warming sensate.

Another embodiment of the present invention is directed to an oral dosage form comprising: a core containing between about 300 mg and about 400 mg acetaminophen, between about 10 mg and about 15 mg diphenhydramine, and between about 2.5 mg and about 7.5 mg phenylephrine; an intermediate coating comprising between about 10 mg and about 20 mg hydroxypropylmethylcellulose and polyethylene glycol; and a fast-release exterior coating comprising: between about 2 mg and about 6 mg hydroxypropylmethylcellulose and polyethylene glycol, between about 3 mg and about 5 mg maltodextrin; and between about 0.5 mg and about 2.5 mg warming sensate.

Additional aspects of the present invention are directed to methods of administering oral dosage forms of the present invention. A user may insert an oral dosage form described herein into their oral cavity and hold it there until they experience a sensate. Upon experiencing the sensate, they may then swallow the oral dosage form. In some embodiments, the oral dosage form may be held in the oral cavity for less than about 10 seconds, or less than about 5 seconds, or less than about 3 seconds, or less than about 2 seconds. The method may further comprising consuming a liquid immediately before or after inserting the oral dosage form in the oral cavity.

Additional aspects of the present invention are directed to methods of treating the symptoms of cold and/or flu, allergies, or nicotine craving comprising administering to a human subject in need thereof an oral dosage form as described herein. In a particular embodiment, the method relates to treating the symptoms of cold and/or flu. Additional aspects of the present invention relates to the use of an oral dosage form as described herein for the treatment of symptoms of cold and/or flu; allergies, or nicotine cravings. In a particular embodiment, the use of an oral dosage form as described herein is for the treatment of symptoms of cold and/or flu. Further embodiments are directed to the oral dosage form described herein for use in the treatment of symptoms of cold and or flu.

EXAMPLES

The following Examples further describe and demonstrate embodiments within the scope of the present invention. The Examples are given solely for the purpose of illustration and are not to be construed as limitations of the present invention. Many variations of these are possible without departing from the spirit and scope of the invention.

Coated Tablet Preparations

Coated caplets having the following formulations were prepared using the following process:

Example 1

| Component | Amount (mg/caplet) |
|---|---|
| Core | |
| Cellulose Microcrystalline (NF) (Avicel-PH102) | 180.7 |
| Acetaminophen 90% Compap SDCrsL | 365.5 |
| Dextromethorphan HBr (USP) | 10 |
| Phenylephrine Hydrochloride (USP) | 5 |
| Croscarmellose Sodium (NF) | 29.75 |
| Silicon Dioxide (NF) | 0.595 |
| Stearic Acid (NF) Food Grade | 2.5 |
| Magnesium Stearate (NF/Ph. Eur.) Veg | 1.5 |
| Intermediate Coating | |
| Opadry Red 15B150006 | 15 |
| Benzoic Acid (USP) | 0.04 |
| Purified Water (USP) [1] | — |
| Exterior Coating | |
| Opadry Red 15B150006 | 4 |
| Maltodextrin M100 | 4 |
| Sucralose Micronized (NF) | 0.3 |
| Polysorbate 60 (NF) (Tween 60) | 1.22 |
| Benzoic Acid (USP) | 0.022 |
| N&A Mint Flavor 535600 T (Firmenich) (approximately 1-10% (w/w) flavor) | 1.55 |
| Warming Sensate 553409 T (Firmenich) (approximately 10-25% (w/w) sensate) | 5.553 |
| Purified Water (USP) [1] | — |

Example 2

| Component | Amount (mg/caplet) |
|---|---|
| Core | |
| Cellulose Microcrystalline (NF) (Avicel-PH102) | 178.2 |
| Acetaminophen 90% Compap SDCrsL | 365.5 |
| Diphenhydramine HCl (USP) | 12.5 |
| Phenylephrine Hydrochloride (USP) | 5 |
| Croscarmellose Sodium (NF) | 29.75 |
| Silicon Dioxide (NF) | 0.595 |
| Stearic Acid (NF) Food Grade | 2.5 |
| Magnesium Stearate (NF/EP) Veg | 1.5 |
| Intermediate Coating | |
| Opadry Blue 15B105013 | 15 |
| Benzoic Acid (USP) | 0.04 |
| Purified Water (USP) [1] | — |

-continued

| Component | Amount (mg/caplet) |
|---|---|
| Exterior Coating | |
| Opadry Blue 15B105013 | 4 |
| Maltodextrin M100 | 4 |
| Sucralose Micronized (NF) | 0.3 |
| Polysorbate 60 (NF) (Tween 60) | 1.22 |
| Benzoic Acid (USP) | 0.022 |
| Purified Water (USP) | — |
| N&A Mint Flavor 535600 T (Firmenich) (approximately 1-10% flavor) | 1.55 |
| Art Sensate 553409 T (Firmenich) (approximately 10-25% sensate) | 5.553 |

Manufacturing Process

Coated caplets having the example formulations were prepared using the following process:

Preparation of Cores

The core ingredients were screened through appropriate sized mesh screening to eliminate clumping and combined into pre-blends to provide adequate distribution of the active ingredients. The pre-blends were then mixed in a V-Blender to produce a Final Blend. The Final Blend was fed into a tablet press, and compressed into tablet cores having the following weight and hardness parameters:

TABLE 1

| Tablet Parameter | Value |
|---|---|
| Hardness | 15 to 21 kp |
| Thickness | 0.218 to 0.242 inches |
| Weight (average) | 0.577 to 0.614 grams |

Tablet Coating

Intermediate Coating

The intermediate coating ingredients were thoroughly blended and sprayed onto the tablet cores using a 60D Accela Cota sprayer under the following conditions:

TABLE 2

| Sprayer Parameter | Value |
|---|---|
| Gun to Bed distance | 10-11 inches |
| Pan speed | 4 rpm |
| Atomizing Air | 55 psi |
| Spray Rate | 680 g/min |
| Inlet Temp | 60° C. |
| Exhaust temp. | 40-50° C. |
| Air flow | 3800 cfm |
| Totalizer | 48.7 L |

Tablets were weighed during coating to ensure that the proper amount of coating was applied.

Exterior Coating

The exterior coating ingredients were thoroughly blended and sprayed onto the tablet cores using a 60D Accela Cota sprayer under the following conditions:

TABLE 3

| Sprayer Parameter | Value |
|---|---|
| Gun to Bed distance | 10-11 inches |
| Pan speed | 4 rpm |
| Atomizing Air | 55 psi |
| Spray Rate | 720 g/min |
| Inlet Temp | 60° C. |

TABLE 3-continued

| Sprayer Parameter | Value |
|---|---|
| Exhaust temp. | 40-50° C. |
| Air flow | 3800 cfm |
| Totalizer | 37.1 L |

Tablets were weighed during coating to ensure that the proper amount of coating was applied.

Example 3—User Testing

Two placebo caplets coated according to Example 1 or Example 2 were tested to determine the onset time of the warming sensate. Below is a summary of the study design, procedure and portions of the study related to onset time of the sensate.

Study Design

Approximately one hundred and fifteen (n=115) healthy male and female adult respondents (between 18-65 years of age) were recruited to provide at least one hundred (n=100) completers.

Each recruited respondent attended two (2) sessions, one session per day. Each session lasted up to 60 minutes in length. In each session, the respondent evaluated two (2) samples and completed a questionnaire for each sample. There was a minimum of 30 minutes rest time in between samples usage. The sample presentation followed a sequential monadic fashion according to a randomized complete block design.

Once successfully re-screened, each individual proceeded to their individual work stations, consumed the sample with a blind 3-digit code, and completed a paper questionnaire. After a 30 minute break, the respondents consumed a second sample and completed the questionnaire. The same process was followed in the second session.

Procedure:

Respondents were instructed to NOT eat or drink (except water) for at least one hour prior to a testing session. The Study Coordinator was responsible for preparing the sample immediately prior to administration. The study coordinator: dispensed the sample (2 caplets) into a 1 oz. dosing cup with the match 3 digit codes and served the sample and water.

During the first half of the session, each respondent received one sample and one instruction. The respondents were asked to read the question, swallow the caplet sample the way they normally swallow a flavored caplet product, or swallow the two caplets at the same time, and answer a paper ballot after they swallow. Room temperature water was provided for those who preferred to swallow with a sip of water.

During the second half of the session, each respondent received one sample and one instruction. The exercise was repeated as in the first half of the session.

Samples and Instructions are as follows:

TABLE 4

| Blinding code | Use Instruction | Formula |
|---|---|---|
| 910 | Use as you normally would use a flavored caplet | A |
| 742 | Please take both flavored caplets at the same time | A |
| 135 | Use as you normally would use a flavored caplet | B |
| 547 | Please take both flavored caplets at the same time | B |

In addition to other questions, each respondent was asked the following question: How fast did you start to experience the warming sensation? The possible answers were as follows:

TABLE 5

| Outcome | Answer |
|---|---|
| Immediately after I used the caplets (about 1-2 seconds) | 1 |
| Shortly after I used the caplets (about 3-10 seconds) Just detectable | 2 |
| Took a while to feel the warming sensation (more than 10 seconds) | 3 |

Results

FIG. 1 shows the results for the question listed above. Regardless of the instructions listed in Table 4, in every instance, the large majority of respondents experienced the sensate in about 1-2 seconds (immediately after using the caplet) with some experiencing the sensate in about 3-10 seconds (shortly after using the caplet) and a small number experiencing the sensate after more than 10 seconds (a while to feel the sensate).

The invention claimed is:

1. A coated oral dosage form that provides a sensorial experience in the oral cavity of the user, comprising:
   a core comprising between about 300 mg and about 400 mg acetaminophen, between about 5 mg and about 15 mg dextromethorphan, and between about 2.5 mg and about 7.5 mg phenylephrine;
   a fast-release exterior coating comprising: between about 2 mg and about 6 mg hydroxypropylmethylcellulose and polyethylene glycol, between about 3 mg and about 5 mg maltodextrin; and between about 0.5 mg and about 2.5 mg warming sensate; and
   an intermediate coating comprising between about 10 mg and about 20 mg hydroxypropylmethylcellulose and polyethylene glycol.

2. The coated oral dosage form of claim 1, wherein the flavoring further comprises a flavor selected from the group consisting of menthol, peppermint, wintergreen, sweet mint, spearmint, vanillin, chocolate, coffee, cinnamon, clove, tobacco, citrus and fruit flavors or mixtures thereof.

3. The coated oral dosage form of claim 1, wherein the fast release exterior coating has a thickness of between about 100 μm and about 100 μm.

4. The coated oral dosage form of claim 3, wherein the fast release exterior coating has a thickness of between about 40 μm and about 80 μm.

5. The coated oral dosage form of claim 1, wherein the fast release exterior coating has a weight of between about 0.5% (w/w) and about 20% (w/w) of the oral dosage form.

6. The coated oral dosage form of claim 1, wherein the core is a caplet.

7. The coated oral dosage form of claim 1, wherein the intermediate coating has a thickness of between about 10 μm and about 100 μm.

8. The coated oral dosage form of claim 1, wherein the coating extends evenly around the entire exterior surface of the oral dosage form.

9. The coated oral dosage form of claim 1, wherein the intermediate coating has a thickness of between about 50 μm and about 70 μm.

10. The coated oral dosage form of claim 7, wherein the intermediate coating has a thickness of between about 50 μm and about 70 μm.

11. The coated oral dosage form of claim 1 comprising dextromethorphan as dextromethorphan bromide in an amount of 10 mg and phenylephrine as phenylephrine hydrochloride in an amount of 5 mg.

12. A method of treating the symptoms of cold and/or flu, and/or allergies comprising administering to a human subject in need thereof a coated oral dosage form as described in claim 1.

13. A coated oral dosage form that provides a sensorial experience in the oral cavity of the user, comprising:
a core comprising between about 300 and about 400 mg acetaminophen, between about 10 mg and about 15 mg diphenhydramine, and between about 2.5 mg and about 7.5 mg phenylephrine;
a fast-release exterior coating comprising between about 2 mg and about 6 mg hydroxypropylmethylcellulose; between about 3 mg and about 5 mg maltodextrin; and between about 0.5 mg and about 2.5 mg of a warming sensate; and
an intermediate coating comprising between about 10 mg and about 20 mg hydroxypropylmethylcellulose.

14. The coated oral dosage form of claim 13 comprising diphenhydramine as diphenhydramine hydrochloride in an amount of 12.5 mg and phenylephrine as phenylephrine hydrochloride in an amount of 5 mg.

15. The coated oral dosage form of claim 13, wherein the flavoring further comprises a flavor selected from the group consisting of menthol, peppermint, wintergreen, sweet mint, spearmint, vanillin, chocolate, coffee, cinnamon, clove, tobacco, citrus and fruit flavors or mixtures thereof.

16. The coated oral dosage form of claim 13, wherein the fast release exterior coating has a thickness of between about 10 μm and about 100 μm.

17. The coated oral dosage form of claim 16, wherein the fast-release exterior coating has a thickness between about 40 μm and about 80 μm.

18. The coated oral dosage form of claim 13, wherein the fast release exterior coating has a weight of between about 0.5% (w/w) and about 20% (w/w) of the oral dosage form.

19. The coated oral dosage form of claim 13, wherein the intermediate coating has a thickness of between about 10 μm and about 100 μm.

20. The coated oral dosage form of claim 19, wherein the intermediate coating has a thickness of between about 50 μm and about 70 μm.

21. The coated oral dosage form of claim 13, wherein the fast release exterior coating extends evenly around the entire exterior surface of the oral dosage form.

22. The coated oral dosage form of claim 13, wherein the core is a caplet.

23. A method of treating the symptoms of cold and/or flu, and/or allergies, comprising administering to a human subject in need thereof a coated oral dosage form as described in claim 13.

24. A coated oral dosage form that provides a sensorial experience in the oral cavity of the user, comprising:
a core comprising between about 300 mg and about 400 mg acetaminophen, between about 5 mg and about 15 mg dextromethorphan, and between about 2.5 mg and about 7.5 mg phenylephrine;
a fast-release exterior coating comprising: between about 2 mg and about 6 mg hydroxypropylmethylcellulose, between about 3 mg and about 5 mg maltodextrin; and between about 0.5 mg and about 2.5 mg warming sensate; and.
an intermediate coating comprising between about 10 mg and about 20 mg hydroxypropylmethylcellulose.

25. The coated oral dosage form of claim 24 comprising dextromethorphan as dextromethorphan bromide in an amount of 10 mg and phenylephrine as phenylephrine hydrochloride in an amount of 5 mg.

26. The coated oral dosage form of claim 24, wherein the fast release exterior coating has a thickness of between about 10 μm and about 100 μm.

27. The coated oral dosage form of claim 24, wherein the fast release exterior coating has a weight of between about 0.5% (w/w) and about 20% (w/w) of the oral dosage form.

28. A coated oral dosage form that provides a sensorial experience in the oral cavity of the user, comprising:
a core comprising between about 300 and about 400 mg acetaminophen, between about 10 mg and about 15 mg diphenhydramine, and between about 2.5 mg and about 7.5 mg phenylephrine;
a fast-release exterior coating comprising between about 2 mg and about 6 mg hydroxypropylmethylcellulose and polyethylene glycol; between about 3 mg and about 5 mg maltodextrin; and between about 0.5 mg and about 2.5 mg of a warming sensate; and
an intermediate coating comprising between about 10 mg and about 20 mg hydroxypropylmethylcellulose and polyethylene glycol.

29. The coated oral dosage form of claim 28 comprising diphenhydramine as diphenhydramine hydrochloride in an amount of 12.5 mg and phenylephrine as phenylephrine hydrochloride in an amount of 5 mg.

30. The coated oral dosage form of claim 28, wherein the intermediate coating has a thickness of between about 10 μm and about 100 μm.

31. The coated oral dosage form of claim 28, wherein the fast release exterior coating has a weight of between about 0.5% (w/w) and about 20% (w/w) of the oral dosage form.

* * * * *